United States Patent [19]

Irons

[11] Patent Number: 4,556,053
[45] Date of Patent: Dec. 3, 1985

[54] KNEE ORTHOSIS WITH LEG STABILIZING MEANS

[75] Inventor: George P. Irons, West Covina, Calif.

[73] Assignee: United States Manufacturing Company, Pasadena, Calif.

[21] Appl. No.: 578,229

[22] Filed: Feb. 8, 1984

[51] Int. Cl.$^4$ .............................................. A61F 5/00
[52] U.S. Cl. ................................... 128/80 C; 128/88
[58] Field of Search .................... 128/80 C, 80 F, 88, 128/87 R

[56] References Cited

U.S. PATENT DOCUMENTS

| | | | |
|---|---|---|---|
| 3,581,741 | 6/1971 | Rosman et al. | 128/80 C |
| 3,898,697 | 8/1975 | Whitehead | 128/80 C |
| 4,337,764 | 7/1982 | Lerman | 128/80 F |

*Primary Examiner*—John D. Yasko
*Attorney, Agent, or Firm*—Christie, Parker & Hale

[57] ABSTRACT

A knee brace comprises generally U-shaped semi-rigid upper and lower cuffs for extending around the upper and lower leg above and below the knee joint; two pairs of upper and lower support arms extending downwardly and upwardly, respectively, from the upper and lower cuff along opposite sides of the patient's leg; and hinges for pivoting the upper support arms to the lower support arms adjacent lateral and medial sides of the knee joint. The upper and lower cuffs encircle the upper and lower legs above and below the knee joint when the brace is fastened to the leg by upper and lower straps located on the brace remote from the knee joint. The upper cuff has downwardly projecting and inwardly movable leg gripping members for contact with the lateral and medial sides of the upper leg immediately above the bony prominences at the lateral and medial sides of the knee joint. An elastic strap attached to the medial leg gripping member of the upper cuff can be tensioned by wrapping the strap behind the leg and around the rigid support arm on the opposite side of the brace and then using the rigid arm for leverage to tension the strap to pull the medial leg gripping member of the upper cuff into pressure contact with the medial side of the upper leg immediately above the knee joint. This produces a wedging action that suspends the brace on the upper leg. The lower cuff has similar upwardly projecting freely bendable leg gripping members and an elastic strap for similarly applying inward pressure to opposite sides of the leg immediately below the knee joint. The upper and lower cuffs are held in intimate contact for a long length of the upper and lower leg, and this in combination with the wedging action of the upper cuff and the firm contact of the lower cuff above and below the knee joint prevents rotation and downward slipping of the knee brace during use.

19 Claims, 6 Drawing Figures

KNEE ORTHOSIS WITH LEG STABILIZING MEANS

FIELD OF THE INVENTION

This invention relates to knee braces, and more particularly to an improved knee brace for supporting the knee to prevent certain motion of the knee joint that could injure the ligaments of the knee, while allowing the knee joint to otherwise bend safely about its axis.

BACKGROUND OF THE INVENTION

A knee brace can be worn by a post-operative patient who has had knee surgery. Knee braces are also worn by persons who suffer knee instabilities or other persons engaged in sporting activities to prevent sporting injuries to the knee. The common purpose of the knee brace is to provide exterior support for the knee to prevent any unnatural movements of the knee joint which could injure or reinjure the knee ligaments, while allowing the normal swinging movement of the knee joint about a horizontal axis through the knee (viz., forward and backward movement of the lower leg or tibia relative to the upper leg or femur, as in a normal walking motion). One type of motion to be prevented by a knee brace is a sudden movement of the upper and lower legs to one side or the other. Another type of motion to be restrained is a twisting or rotation of the lower leg relative to the upper leg about a vertical axis.

Several such knee braces have been developed in recent years. These prior art knee braces include the braces disclosed in U.S. Pat. No. 3,669,105 to Castiglia and U.S. Pat. No. 4,372,298 to Lerman. The Castiglia brace has a pair of lateral uprights extending along the outside of the leg and articulated at the outside of the knee joint by a single axis pivot pin. Upper and lower contact pads attached to the ends of the uprights contact the outside of the thigh and lower leg above and below the knee joint. Curved rigid bars extend from the upper and lower contact pads around and in front of the upper and lower leg to the inside of the knee joint where the ends of the curved bars are interconnected by another single axis pivot pin. A condyle pad attached to the inside pivot pin engages the inside of the patient's knee joint. The pad rotates about the pivot pin axis independently of the upper and lower curved bars. A pair of wide elastic rubber straps attached to the upper and lower contact pads encircle the leg above and below the knee joint to support the curved bars on the upper leg and lower leg. A smaller elastic strap is attached to the lower contact pad and is spiralled upwardly around the back of the knee and attaches to the upper contact pad. This elastic strap provides a de-rotation capability for preventing the lower leg from rotating or twisting relative to the upper leg about a vertical axis.

The knee brace disclosed in the patent to Lerman has upper and lower U-shaped supports for the upper leg and the lower leg and two pairs of upper and lower support arms extending along the lateral and medial sides of the patient's leg between the upper and lower supports. The support arms pivot about a polycentric pivot joint adjacent the lateral and medial sides of the knee joint. Upper and lower flexible elastic straps secured to the upper and lower supports extend around the upper and lower leg for attaching the knee brace to the leg. Condyle pads inside the polycentric pivots apply pressure to the lateral and medial sides of the knee joint. Upper and lower elastic straps adjacent the condyle pads wrap around the knee joint for holding the condyle pads in contact with the lateral and medial sides of the patient's knee joint.

The Lerman knee brace is an improvement over the Castiglia brace in the sense that the Lerman brace is more comfortable, in part, because it eliminates pressure points at the front of the legs. The Lerman brace also provides better overall contact with both sides of the knee joint, by providing the lateral and medial condyle pads which are held in pressure contact with the knee joint through the full range of motion at the knee. However, both of these knee braces must be held in the proper fixed position around the patient's knee in order to provide the required support throughout the full range of motion at the knee. Thus, there is a need to provide a knee brace which can maintain the required support through constant use of the brace. Some braces currently used today have a tendency to twist about the leg or slip down along the leg while the brace is worn. This, of course, disrupts the support which must be carefully controlled during use. Knee supporting braces are often fitted by an orthotist who carefully shapes the brace to the patient's leg. In fact, the Castiglia brace is custom fitted to a plaster cast of the patient's leg. Thus, any deviation from the necessary positioning of the brace on the leg should be avoided.

SUMMARY OF THE INVENTION

This invention provides a knee brace with an improved means of attaching the brace to the leg to prevent the brace from twisting or slipping down on the leg during use.

Briefly, one embodiment of the knee bace of this invention includes upper and lower limb support members, a pair of upper support arms extending down from the upper limb support member for extending along opposite sides of the upper leg to remote ends adjacent lateral and medial sides of the knee joint, a pair of lower support arms extending upwardly from the lower limb support member for extending along opposite sides of the lower leg to remote ends adjacent lateral and medial sides of the knee joint, and lateral and medial pivot means connecting remote ends of the upper support means with corresponding remote ends of the lower support arms for providing relative pivotal movement of the upper and lower support arms so they pivot about a generally horizontal axis adjacent the lateral and medial sides of the knee joint. The upper support members are in the form of a generally U-shaped semi-rigid cuff, and opposite side portions of the upper cuff are rigidly fixed to the lateral and medial upper support arms. Bendable lateral and medial free end portions of the upper cuff extend in the same general direction away from the lateral and medial upper support arms. Downwardly projecting opposite lower side portions of the upper cuff are unsupported on the adjacent support arms so that they can bend inwardly into the space between the lateral and medial pivot means. A flexible strap is carried on a bendable portion of the cuff so that the strap can be tensioned to pull the bendable lower side portions of the cuff into pressure contact with opposite sides of the upper leg immediately above the bony prominences at the lateral and medial sides of the knee joint. This wedges the upper cuff to the leg and ensures that the knee brace will not twist or slide down on the leg during use.

In another embodiment, the lower support is in the form of a generally U-shaped semi-rigid cuff rigidly affixed at opposite sides to the lower support arms. Bendable lateral and medial fee end portions of the lower cuff extend in the same direction away from the lateral and medial lower support arms. Upwardly projecting opposite upper side portions of the lower cuff are unsupported on the adjacent lower support arms so that they can bend inwardly into the space between the lateral and medial pivot means. A flexible strap carried on a bendable upper portion of the lower cuff can be tightened to bend the upper side portions of the lower cuff into pressure contact around the lower leg immediately below the knee joint. The upper and lower cuffs combine to provide an elongated means of support on the upper and lower leg that can be tightened to provide circumferential contact with the upper and lower leg above and below the knee joint to enhance the amount of contact with the leg which, in turn, assists in preventing migration of the knee brace during use.

These and other aspects of the invention will be more fully understood by referring to the following detailed description and the accompanying drawings.

DRAWINGS

DETAILED DESCRIPTION

Figure 1:
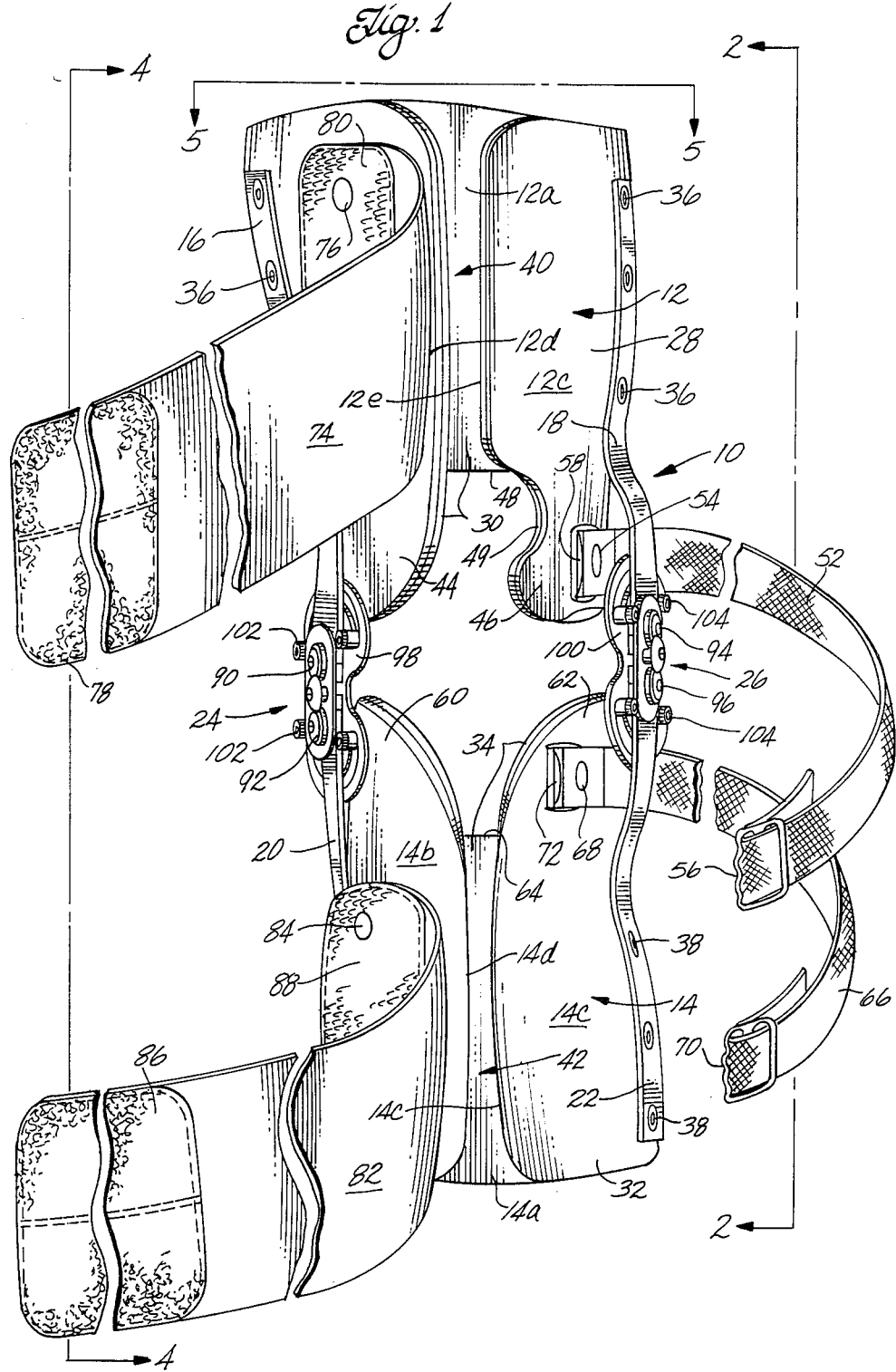
FIG. 1 is a fragmentary front elevation view showing a knee orthosis according to principles of this invention.
Figure 2:
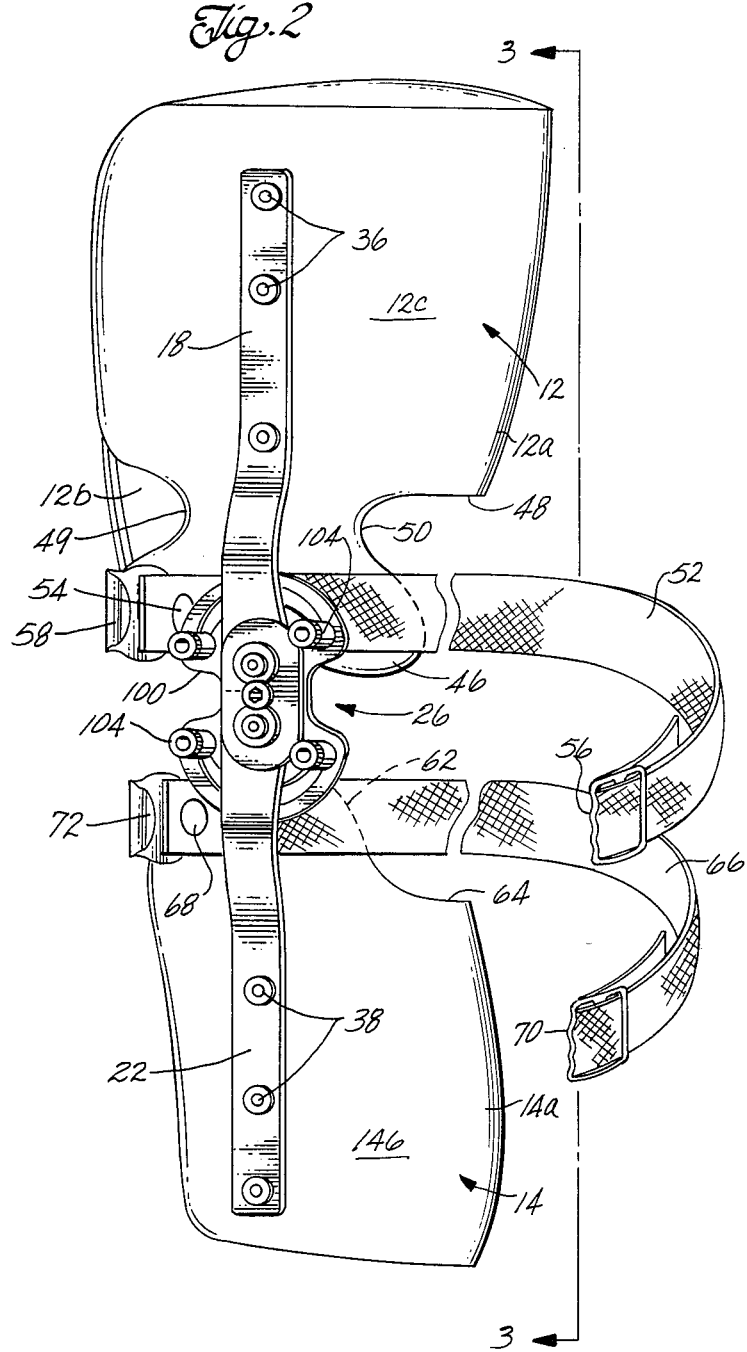
FIG. 2 is a side elevation view taken on line 2—2 of FIG. 1 showing the medial side of the orthosis.
Figure 3:
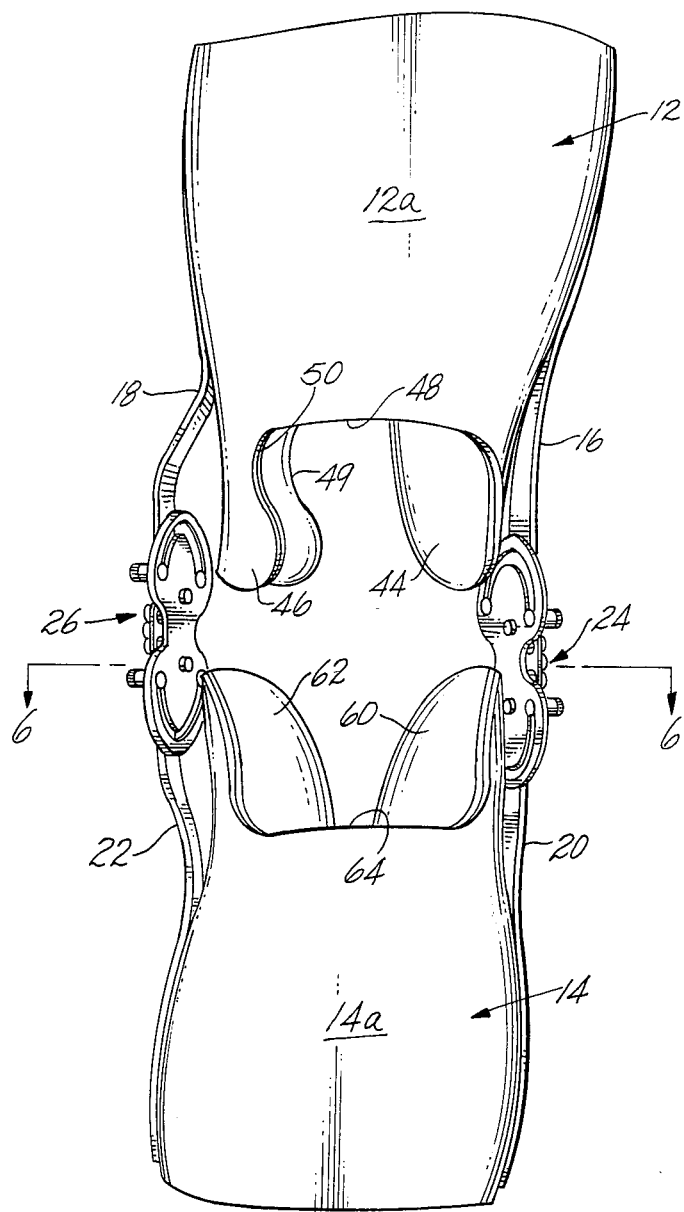
FIG. 3 is a rear elevation view taken on line 3—3 of FIG. 2 showing the back side of the orthosis.
Figure 4:
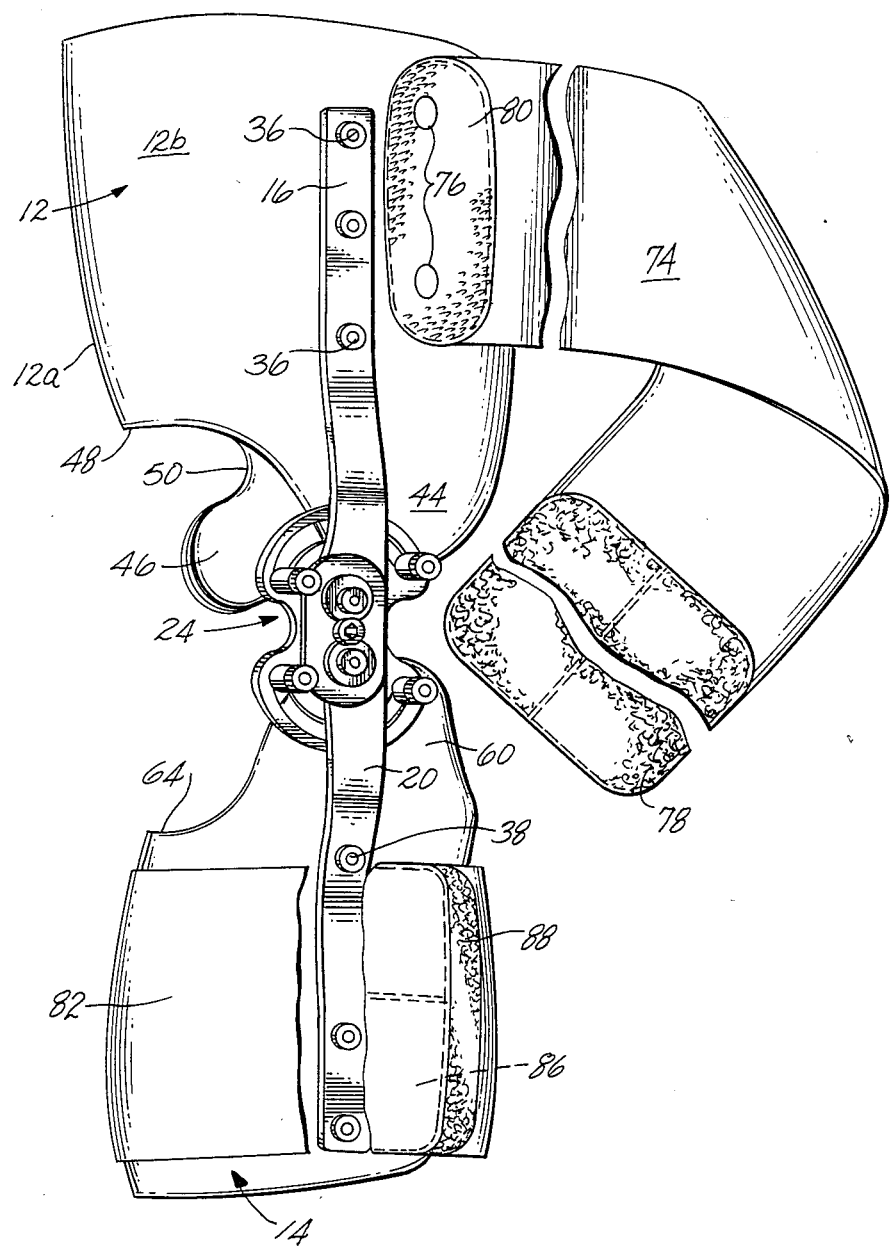
FIG. 4 is a fragmentary side elevation view taken on line 4—4 of FIG. 1 showing the lateral side of the orthosis.
Figure 5:
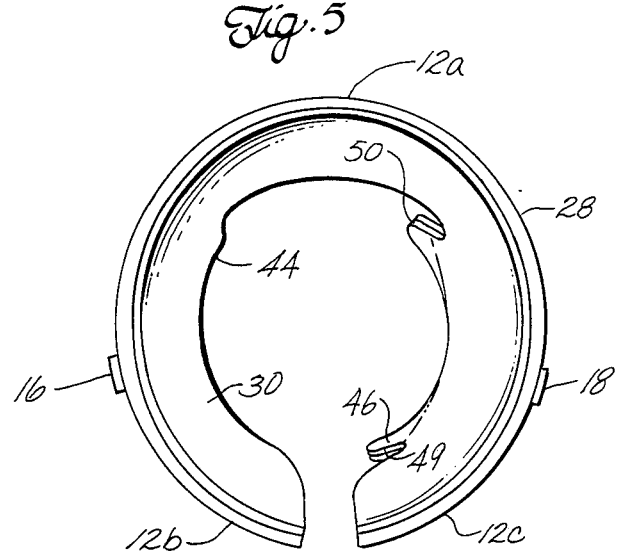
FIG. 5 is a top view taken on line 5—5 of FIG. 1.
Figure 6:
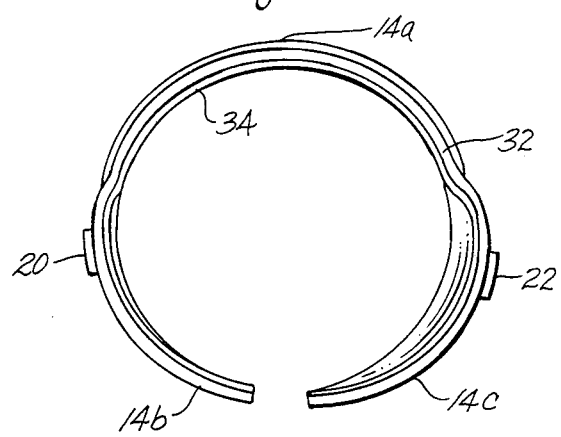
FIG. 6 is a top view taken on line 6—6 of FIG. 3.

The drawings illustrate a knee brace 10 constructed according to the principles of this invention for supporting the ligaments of the knee. As shown best in FIG. 1, the knee brace includes a generally U-shaped upper cuff 12 and a generally U-shaped lower cuff 14 spaced below the upper cuff. A pair of horizontally spaced apart rigid elongated lateral and medial upper support arms 16 and 18, respectively, are affixed to lateral and medial sides of the upper cuff. The upper support arms extend downwardly toward a horizontal rotational axis which extends from side to side through the knee joint. The knee joint, for simplicity, can be considered to provide rotation about a single horizontal axis; although in reality the knee joint provides rotation about a polycentric axis. A pair of horizontally spaced apart rigid elongated lateral and medial lower support arms 20 and 22, respectively, are affixed to lateral and medial sides of the lower U-shaped cuff 14. The lower support arms extend upwardly toward the horizontal rotational axis through the knee joint. The ends of the upper and lower arms on the lateral and medial sides of the knee joint are interconnected by corresponding lateral and medial polycentric hinges 24 and 26, respectively. The hinges allow the upper and lower support arms on both sides of the brace to swing in unison about a polycentric axis through the knee joint.

The upper cuff 12 has an outer face 28 made of a thin semi-rigid bendable plastic piece preferably of low density polyethylene. The upper cuff also has a resilient inner layer 30 of a closed cell polymeric material such as polyethylene or polyurethane, although open cell plastic foam materials also can be used as the resilient inner layer. The lower cuff 14 also has an outer face 32 of a similar thin semi-rigid bendable plastic material and an inner resilient layer 34 of padding made from the same plastic foam material.

The opposite lateral and medial sides of the upper cuff are rigidly affixed to the lateral and medial upper support arms by fasteners 36, and the opposite lateral and medial sides of the lower cuff 32 are similarly rigidly affixed to the lateral and medial lower support arms 20 and 22 by fasteners 38. The upper cuff extends for a sufficient distance in the upright direction so that the cuff can wrap around the upper leg (femur) from immediately above the knee joint to about half way up the thigh. The upper cuff is sufficiently bendable to be wrapped tightly around this region of the thigh. Similarly, the lower cuff extends for a sufficient distance in the upright direction to be wrapped around the lower leg (tibia) from immediately below the knee joint to about half way down the tibia. The lower cuff is also sufficiently bendable to be wrapped tightly around this region of the lower leg.

The upper cuff 12 has a continuous U-shaped rear half 12a that extends behind the upper leg between the lateral and medial support arms. Bendable free end portions 12b and 12c on lateral and medial sides of the upperr cuff extend forwardly away from the lateral and medial upper support arms 16 and 18.

Likewise, the lower cuff 14 has a continuous U-shaped rear half 14a that extends behind the lower leg between the lateral and medial lower support arms. Bendable lateral and medial free end portions 14b and 14c of the lower cuff extend forwardly away from the lateral and medial lower support arms 20 and 22.

The bendable lateral and medial free end portions 12b and 12c of the upper cuff project away from the upper support arms sufficiently so that the upper cuff can extend around essentially the entire circumference of the thigh when the orthosis is used. The upper cuff has confronting upright marginal front edges 12d and 12e extending uprightly at the lateral and medial bendable free end portions of the upper cuff. This leaves a narrow upright opening 40 normally extending between these confronting edges along the front of the upper cuff. In a similar manner the bendable lateral and medial free end portions 14b and 14c of the lower cuff extend away from the lower support bars by a distance sufficient so that the lower cuff can extend essentially around the entire circumference of the lower leg when the orthosis is used. The free ends of the lower cuff have confronting lateral and medial upright edges 14d and 14e, leaving a narrow opening 42 extending uprightly along the front center of the lower cuff.

The opposite sides of the upper cuff have inwardly bendable lateral and medial leg gripping members 44 and 46, respectively. These can also be referred to as lateral and medial condylar portions of the upper cuff. These leg gripping members project downwardly below a horizontal bottom edge 48 extending across the rear half of the upper cuff. The upper side portions of the upper cuff are rigidly affixed to the lateral and medial support arms 16 and 18. The downwardly projecting leg gripping members 44 and 46 are not fastened to the adjacent support arms and are therefore freely bendable inwardly into the open space between the upper support arms. The outer edge of the lateral leg gripping member 44 has a U-shaped curvature from front to rear.

Only the bottom edge of the medial leg gripping member has a U-shaped curvature. Front and rear edges 49 and 50 of the medial leg gripping member 46 are recessed inwardly to add flexibility to the medial leg gripping member. The lateral and medial leg gripping members extend to a location where they can apply inward pressure to opposite sides of the leg immediately above the bony prominences at the lateral and medial sides of the upper leg above the knee joint.

An elongated flexible upper elastic strap 52 is affixed to the outer face of the flexible medial leg gripping member 46. The elastic strap is affixed to the cuff by a fastener 54. The elastic strap has an axially adjustable clip 56 adjacent its free end. A fixed hook 58 is attached to the upper strap adjacent the strap's point of connection to the cuff.

The opposite sides of the lower cuff have inwardly bendable lateral and medial leg gripping members 60 and 62, respectively. These leg gripping members, which can also be referred to as condylar portions of the lower cuff, project upwardly above a horizontal upper edge 64 extending across the rear half of the lower cuff. The lower side portions of the lower cuff are rigidly affixed to the lower lateral and medial support arms. The upwardly projecting leg gripping members 60 and 62 are not fastened to the adjacent support arms and are therefore freely bendable inwardly into the open space between the lower support arms. The outer edges of the lower leg gripping members are both of U-shaped curvature from front to rear. The curved upper edges of the lower leg gripping members extend upwardly to an elevation slightly closer to the axis of rotation of the brace than the bottom edges of the upper leg gripping members. The lower lateral and medial leg gripping members extend to a location where they can apply inward pressure to opposite sides of the lower leg immediately below the bony prominences at the lateral and medial sides of the lower leg below the knee joint.

An elongated flexible lower elastic strap 66 is affixed to the outer face of the flexible medial lower leg gripping member 62. The lower strap is affixed to the lower cuff by a fatener 68. The lower elastic strap has an axially adjustable clip 70 at its free end. A fixed hook 72 is attached to the lower strap adjacent the strap's point of connection to the lower cuff.

A flexible elongated upper strap 74 is secured to the outer face of the upper cuff by fasteners 76. Cooperating thistle cloth fasteners, such as the material sold under the trademark Velcro, are attached to the outer face of the upper cuff, adjacent the upper strap's point of attachment to the upper cuff, and to the inside face of the upper strap adjacent the free end of the strap. In the illustrated embodiment, a fastener 78 of a pile type Velcro material is affixed to the free end of the upper strap, and a fastener of hook type Velcro material 80 is affixed to the outer face of the upper strap at its point of attachment to the upper cuff. Similarly, a lower flexible elongated lower strap 82 is secured to the outer face of the lower cuff by fasteners 84. A thistle cloth fastener 86 of a pile material is affixed to the inside face of the lower strap at its free end, and a cooperating thistle cloth fastener 88 of a hook material is secured to the outer face of the strap adjacent its point of attachment to the lower cuff. The upper and lower straps are preferably made from an elastically stretchable material such as gum rubber so the straps can be stretched to fit tightly around the patient's upper and lower leg. The upper and lower straps are preferably affixed to the bendable forwardly projecting lateral free end portions 12b and 14b of the upper and lower cuff.

The lateral and medial polycentric hinges 24 and 26 are known in the art. In each polycentric hinge the lower end of each upper support arm has gear teeth that mesh with cooperating gear teeth on the upper end of the adjacent lower support arm. The interconnected gear teeth provide polycentric hinges that allow the upper support arms to pivot in unison through an angle relative to the lower support arms about a horizontal polycentric axis through the knee joint. The cooperating gears of the polycentric hinges make it possible for the lower support arms to pivot automatically when the upper support arms pivot, and vice versa. The polycentric hinge on the lateral side includes a lateral upper pivot pin 90 and a lateral lower pin 92, and the polycentric hinge on the medial side includes a medial upper pivot pin 94 and a medial lower pivot pin 96. The polycentric hinges also include a lateral stop bracket 98 and a medial stop bracket 100 as portions of adjustable motion stops for controlling the angles of rotation of the upper support arms and the lower support arms. This type of adjustable motion stop is known in the art and is known as the Lerman orthotic joint sold by U.S. Manufacturing Company, the assignee of this application. The adjustable motion joint is also disclosed in U.S. Pat. No. 4,337,764 which is also assigned to the assignee of this application. The adjustable motion joints include stops 102 on the lateral side of the brace and stops 104 on the medial side of the brace.

In use, the knee brace is placed around the knee joint of a patient by first placing the upper and lower legs of the patient within the upper and lower cuffs so the inside faces of the upper and lower cuffs are in contact circumferentially with the patient's upper and lower leg. The bendable free ends of the upper and lower cuffs and the length of the cuffs enhance the area of contact. The brace is positioned so the polycentric hinges are closely aligned with the horizontal side-to-side pivot axis through the patient's knee joint. The upper and lower straps are then stretched longitudinally and can be tightly wrapped around the patient's upper and lower legs for securing the upper and lower cuffs to the patient's upper and lower legs above and below the knee joint. It may be desirable to place the leg gripping portions of the cuffs in their desired contact with the opposite sides of the knee joint before fully tightening the upper and lower straps. The upper strap is attached only to the upper portion of the upper cuff and the lower strap is attached only to the lower portion of the lower cuff. Therefore, by tightening the straps around the patient's uppper and lower leg, only the upper portion of the upper cuff and the lower portion of the lower cuff are drawn into close contact with the patient's leg. The upper and lower straps are stretchable and therefore can apply a substantial amount of circumferential pressure to the patient's upper and lower legs when the two straps are stretched. The straps are wrapped tightly around the exterior of the upper and lower cuffs and the thistle cloth fasteners at the free ends of the straps are then attached to the cooperating fasteners on the same straps to retain the amount of circumferential pressure applied by the stretched upper and lower straps. The bendable leg gripping members 12b and 12c of the upper cuff are placed in contact with the lateral and medial sides of the leg above the knee joint. The medial elastic strap 52 at the bottom of the upper cuff is then wrapped behind the patient's leg and around the outside of the lateral support arm 16 and then wrapped around in front of the patient's leg. The clip 56 is then fastened to the hook 58 to securely hold the leg gripping members 12b and 12c in firm contact with opposite sides of the patient's knee joint. The elastic strap is stretchable; and the fasteners 56 and 58 are adjusted to that, when fastened, they retain a substantial amount of inward pressure on opposite sides of the patient's leg, through the opposing inwardly pulled leg gripping members. The strap is wrapped around the outside of the upper lateral support arm to provide a rigid and stationary means of applying leverage to the strap for pulling the flexible upper medial leg gripping member 46 into the knee. This produces a wedging action which applies inward pressure constantly to the patient's upper leg immediately above the bony prominence on the medial side of the knee joint to securely hold the upper cuff on the patient's upper leg. This wedging action of the bendable lower portions of the upper cuff combined with the intimate contact produced by the long length of the upper cuff entirely surrounding the patient's upper leg resists twisting of the brace about the axis of the leg and also prevents the brace from sliding downwardly on the leg during use.

After the upper cuff is attached to the upper leg the elastic strap 66 on the lower cuff also is wrapped behind the lower cuff and the patient's lower leg and around the lower lateral support arm 20 and the leverage of that support arm can be used for applying tension to the strap to pull the flexible medial leg gripping portion 62 of the lower cuff into close contact with the patient's lower leg immediately below the knee joint. Inward pressure also is applied to the lower leg by the lateral leg gripping member 60. After the elastic straps have been wrapped around the patient's leg and tightened to hold the leg gripping members in contact with opposite sides of the patient's leg above and below the knee joint, the upper and lower straps 74 and 82 then can be tensioned to their fullest extent for securely holding the fixed upper and lower portions of the upper and lower cuffs on the patient's upper and lower legs.

The upper and lower straps 74 and 82 are wrapped around the patient's leg in a direction for applying torque in one direction of rotation around the patient's leg. The elastic straps 52 and 66 are wrapped in an opposite direction around the patient's leg to apply torque through the cuffs to the patient's leg in an opposite direction of rotation.

The knee brace of this invention produces total contact with the upper and lower leg through the bendable upper and lower cuffs, which enhances stability. The upper and lower cuffs also are padded to provide comfort in addition to the imroved stability. The cuffs also provide good rotational control. Moreover, their overall length is sufficiently long to produce good leverage and good protection to the knee. The medial femoral condylar gripping member and the high medial wall on the lower cuff provide good medial/lateral stability. The condylar leg gripping members also aid in suspension, preventing distal migration. The elastic straps above and below the knee also control recurvatum and anterior drawing.

What is claimed is:

1. A knee brace comprising:

upper and lower limb support members;

means for securing the upper and lower limb support members to the upper and lower legs of a patient above and below the knee joint;

a pair of rigid upper support arms extending down from the upper limb support member for extending along opposite sides of the upper leg to remote ends adjacent lateral and medial sides of the knee joint;

a pair of rigid lower support arms extending upwardly from the lower limb support member for extending along opposite sides of the lower leg to remote ends adjacent lateral and medial sides of the knee joint;

medial and lateral pivot means defining an axis of rotation through the knee joint and connecting the remote ends of the upper support arms with the remote ends of corresponding lower support arms for providing relative pivotal movement of the upper and lower support arms adjacent the lateral and medial sides of the knee joint;

means rigidly attaching medial and lateral upper portions of the upper limb support member to the upper support arms;

the upper limb support member being in the form of a generally U-shaped and elongated upper cuff for wrapping around the patient's upper leg above the knee joint, with bendable elongated lateral and medial lower portions of the upper cuff freely extending downwardly from the rigid attaching means for being movable toward an open central region of the brace away from the rigid upper support arms and into contact with the lateral and medial sides of the upper leg immediately above the bony prominences at the lateral and medial sides of the knee joint;

tensioning means attached to such bendable lower portion of the upper cuff at an elevation spaced above said axis of rotation for being wrapped around the patient's leg and around the upper support arm on the opposite side of the brace and then tensioned using the opposite support arm of the brace as a means of applying leverage to the tensioning means for pulling the lateral and medial bendable lower portions of the upper cuff inwardly away from the adjacent support arms and into pressure contact with the lateral and medial sides of the leg immediately above the bony prominences at the lateral and medial sides of the upper leg above the knee joint; and means for retaining tension applied by the tensioning means to maintain the inward pressure contact applied by the bendable lower portions of the upper cuff for suspending the knee brace on the upper leg to prevent rotation of the knee brace about the axis of the leg and to prevent the knee brace from slipping downwardly on the leg.

2. Apparatus according to claim 1 in which the tensioning means is attached to the bendable medial lower portion of the upper cuff.

3. Apparatus according to claim 2 in which the freely bendable medial lower portion of the upper cuff is recessed in its width at an elevation thereon spaced above the bottom edge of said medial lower portion to add flexibility to that portion of the upper cuff.

4. Apparatus according to claim 1 in which the upper and lower limb support members are each in the form of U-shaped upper and lower cuffs each of which is rigidly affixed to the lateral and medial support arms on opposite sides of the U, and each of which has elongated bendable free end portions projecting toward the pivot means and away from the points of attachment to the adjacent support arms; and in which the bendable free ends of each cuff are movable away from their adjacent support arms for contact with adjacent sides of the upper and lower leg at elevations spaced from the knee joint.

5. Apparatus according to claim 4 in which the lower cuff has inwardly bendable upwardly projecting lateral and medial portions for being movable into contact with lateral and medial sides of the lower leg immediately below the knee joint, and lower tensioning means attached to one of the bendable upper portions of the lower cuff for being wrapped around the leg and around the lower support arm on the opposite side of the brace for applying leverage to the lower tensioning means to pull the bendable upper portions of the lower cuff inwardly into pressure contact with opposite sides of the lower leg.

6. Apparatus according to claim 5 including means for retaining the inward pressure applied by the bendable upper portions of the lower cuff.

7. Apparatus according to claim 3 in which the bottom edge of the freely bendable medial lower portion of the upper cuff is spaced above the axis of rotation through the medial and lateral pivot means.

8. Apparatus according to claim 1 in which the bendable lower portions of the upper cuff project downwardly below a transverse bottom edge of the upper cuff extending across the upper cuff between the lateral and medial upper support arms of the brace.

9. A knee brace comprising:
upper and lower limb support members;
means for securing the upper and lower limb support members to the upper and lower legs of a patient above and below the knee joint;
a rigid upper support arm extending down from the upper limb support member along the medial side of the upper leg of a patient to a remote end adjacent the medial side of the knee joint;
a rigid lower support arm extending upwardly from the lower limb support member along the lower leg of the patient to a remote end adjacent the medial side of the knee joint;
pivot means connecting the remote ends of the upper and lower support arms for defining an axis of rotation through the knee joint and providing relative pivotal movement of the support arms about said axis adjacent the medial side of the knee joint;
means rigidly attaching an upper medial side portion of the upper limb support member to the upper support arm;
the upper limb support member being in the form of a generally U-shaped and elongated upper cuff for wrapping around the patient's upper leg spaced above the knee joint, the upper cuff having a bendable and elongated medial lower portion freely extending downwardly from the means of rigidly attaching the medial side of the upper limb support member to the upper support arm, the freely bendable medial lower portion of the upper cuff being movable inwardly away from the upper support arm and toward an open central region of the brace, the bendable medial lower portion of the cuff having a reduced width at an elevation spaced above a bottom edge of said medial lower portion to add flexibility to that portion of the cuff;
tensioning means attached to the bendable medial lower portion of the upper cuff at an elevation spaced above said axis of rotation so that the tensioning means can be tensioned for pulling the bendable medial lower portion of the upper cuff inwardly away from the upper support arm and into pressure contact with the medial side of the leg immediately above the bony prominence at the medial side of the upper leg above the knee joint; and
means for retaining tension applied by the tensioning means to maintain the inward pressure contact applied to the medial side of the leg by the bendable medial lower portion of the upper cuff for suspending the knee brace on the upper leg to prevent rotation of the knee brace about the axis of the leg and to prevent the knee brace from slipping downwardly on the leg.

10. Apparatus according to claim 9 in which the reduced width portion of the medial lower portion of the upper cuff has recessed front and rear edges spaced above the bottom edge of the medial lower portion of the cuff, and in which the recessed portions of the cuff are at an elevation spaced above the rotational axis of the knee joint defined by the pivot means.

11. Apparatus according to claim 10 in which the tensioning means are attached to the bendable medial lower portion of the cuff below said recessed front and rear edges of the cuff.

12. Apparatus according to claim 9 in which the bottom edge of the freely bendable medial lower portion of the upper cuff is at an elevation spaced above the rotational axis of the pivot means, so that the retained tension on the tensioning means holds the bottom edge of the medial lower portion of the cuff in pressure contact with the patient's upper leg immediately above the bony prominence on the medial side of the leg above the knee joint.

13. A knee brace comprising:
upper and lower limb support members;
means for securing the upper and lower limb support members to the upper and lower edges of a patient above and below the knee joint;
a pair of rigid upper support arms extending down from the upper limb support members for extending along opposite sides of the upper leg to remote ends adjacent lateral and medial sides of the knee joint;
a pair of rigid lower support arms extending upwardly from the lower limb support member for extending along opposite sides of the lower leg to remote ends adjacent lateral and medial sides of the knee joint;
medial and lateral pivot means defining an axis of rotation through the knee joint and connecting the remote ends of the upper support arms with the remote ends of the corresponding lower support arms for providing relative pivotal movement of the upper and lower support arms adjacent the lateral and medial sides of the knee joint;
upper fastening means rigidly attaching upper portions of the upper limb support member to the upper support arms;
the upper limb support member being in the form of a generally U-shaped and elongated upper cuff for wrapping around the patient's upper leg above the knee joint, with bendable elongated lateral and medial lower portions of the upper cuff freely extending downwardly from the upper fastening means for being movable toward an open central region of the brace away from the lateral and medial upper support arms and into contact with the lateral and medial sides of the upper leg, respectively; the freely bendable lateral and medial lower portions of the upper cuff projecting downwardly below a transverse bottom edge of the U-shaped upper cuff which extends between the lateral and medial support arms for enhancing flexibility of the inwardly bendable lateral and medial lower portions of the upper cuff;

lower fastening means rigidly attaching lower portions of the lower limb support member to the lower support arms;

the lower limb support member being in the form of a generally U-shaped and elongated lower cuff for wrapping around the lower leg below the knee joint, with bendable elongated lateral and medial upper portions of the lower cuff extending freely upwardly from the lower fastening means for being movable toward an open central region of the brace away from the lateral and medial lower support arms and into contact with the lateral and medial sides of the lower leg immediately below the knee joint, the freely bendable upper portions of the lower cuff extending upwardly above a transverse upper edge of the U-shaped lower cuff which extends between the lateral and medial lower support arms for enhancing flexibility to the bendable upper portions of the lower cuff;

upper tensioning means attached to at least one of said bendable lower portions of the upper cuff for being wrapped around the patient's leg and around the upper support arm on the opposite side of the brace and then tensioned using the opposite rigid support arm of the brace as a means of applying leverage to the upper tensioning means for pulling the lateral and medial bendable lower portions of the upper cuff inwardly away from the adjacent upper support arms and into pressure contact with the lateral and medial sides of the leg immediately above the knee joint;

means for retaining tension applied by the upper tensioning means to maintain the inward pressure contact applied by the bendable lower portions of the upper cuff for suspending the upper cuff of the knee brace on the upper leg to prevent rotation of the knee brace about the axis of the leg and to prevent the knee brace from slipping downwardly on the leg;

lower tensioning means attached to at least one of said bendable upper portions of the lower cuff for being wrapped around the patient's leg and around the lower support arm on the opposite side of the brace and then tensioned using the opposite rigid support arm of the brace as a means of applying leverage to the lower tensioning means for pulling the lateral and medial bendable upper portions of the lower cuff inwardly away from the adjacent lower support arms and into pressure contact with the lateral and medial sides of the leg immediately below the knee joint; and means for retaining tension applied by the lower tensioning means to maintain the inward pressure contact applied by the bendable upper portions of the lower cuff for securely holding the lower cuff around the patient's lower leg.

14. Apparatus according to claim 13 in which the upper and lower tensioning means are attached to the medial sides of the freely bendable lower and upper portions of the upper and lower cuffs, respectively.

15. Apparatus according to claim 13 in which the bendable medial lower portion of the upper cuff is recessed in its width at an elevation spaced above the bottom edge of the upper cuff to enhance the flexibility of that portion of the upper cuff so that tensioning of the upper tensioning means can apply pressure to the bony prominence immediately above the medial side of the knee joint.

16. Apparatus according to claim 13 in which bottom edges of the bendable lateral and medial lower portions of the upper cuff are spaced above the axis of rotation through the lateral and medial pivot means; and in which upper edges of the bendable lateral and medial upper portions of the lower cuff are spaced below said axis of rotation, for use in maintaining the bottom and upper edges of the upper and lower cuffs, respectively, in pressure contact with the bony prominences on the lateral and medial sides of the upper and lower leg.

17. A knee brace comprising:
upper and lower limb support members;
means for securing the upper and lower limb support members to the upper and lower legs of a patient above and below the knee joint;
a rigid upper support arm extending down from the upper limb support member along the medial side of the upper leg of a patient to a remote end adjacent the medial side of the knee joint;
a rigid lower support arm extending upwardly from the lower limb support member along the lower leg of the patient to a remote end adjacent the medial side of the knee joint;
pivot means connecting the remote ends of the upper and lower support arms for defining an axis of rotation through the knee joint and providing relative pivotal movement of the support arms about said axis adjacent the medial side of the knee joint;
means rigidly attaching an upper medial side portion of the upper limb support member to the upper support arm;
the upper limb support member being in the form of a generally U-shaped and elongated upper cuff for wrapping around the patient's upper leg above the knee joint, the upper cuff having a bendable and elongated medial lower portion freely extending downwardly from the means of rigidly attaching the medial side of the upper limb support member to the upper support arm, the freely bendable medial lower portion of the upper cuff being movable inwardly away from the upper support arm and toward an open central region of the brace, the bendable lower portion of the cuff having a bottom edge which terminates at an elevation spaced above the rotational axis through the pivot means;
tensioning means attached to the bendable medial lower portion of the upper cuff at an elevation spaced above said axis of rotation so that the tensioning means can be tensioned for pulling the bendable medial lower portion of the cuff inwardly away from the upper support arm and into pressure contact with the medial side of the leg immediately above the bony prominence at the medial side of the upper leg above the knee joint; and
means for retaining the tension applied by the tensioning means to maintain the inward pressure contact applied to the medial side of the upper leg by the bendable lower portion of the cuff, so that retained tension on the tensioning means holds the bottom edge of the medial lower portion of the upper cuff in constant inward pressure contact with the patient's upper leg immediately above the bony prominence on the medial side of the leg above the knee joint for stabilizing the upper cuff on the patient's upper leg.

18. Apparatus according to claim 17 in which the freely bendable medial lower portion of the upper cuff has recessed front and rear edges spaced above the bottom edge of the medial lower portion of the cuff for enhancing flexibility of that portion of the cuff.

19. Apparatus according to claim 17 in which the tensioning means are attached to a region of the freely bendable lower medial portion of the upper cuff below the recessed portions thereof.

* * * * *